(12) United States Patent
Jüstel et al.

(10) Patent No.: US 7,288,107 B2
(45) Date of Patent: Oct. 30, 2007

(54) TANNING DEVICE

(75) Inventors: Thomas Jüstel, Aachen (DE); Cornelis Ronda, Aachen (DE); Franscisus Altena, Roosendaal (NL); Wolfgang Busselt, Roetgen (DE); Olaf Mastenbroek, Groes (NL); Hans-Helmut Bechtel, Roetgen (DE)

(73) Assignee: Koninklijke Philips Electronics, N.V., Eindhoven (NL)

( * ) Notice: Subject to any disclaimer, the term of this patent is extended or adjusted under 35 U.S.C. 154(b) by 61 days.

(21) Appl. No.: 10/520,496

(22) PCT Filed: Jul. 2, 2003

(86) PCT No.: PCT/IB03/03107

§ 371 (c)(1),
(2), (4) Date: Jan. 7, 2005

(87) PCT Pub. No.: WO2004/008485

PCT Pub. Date: Jan. 22, 2004

(65) Prior Publication Data

US 2005/0261751 A1    Nov. 24, 2005

(30) Foreign Application Priority Data

Jul. 11, 2002  (DE) .................... 102 31 257

(51) Int. Cl.
*A61N 5/06* (2006.01)
*H61J 63/02* (2006.01)

(52) U.S. Cl. ............. 607/90; 607/88; 607/94; 313/485; 313/486

(58) Field of Classification Search ............ 607/88, 607/90–95; 313/483–487; 362/84, 217, 362/223–225, 227, 260, 263; 250/481.3, 250/494.1
See application file for complete search history.

(56) References Cited

U.S. PATENT DOCUMENTS

| | | | | |
|---|---|---|---|---|
| 4,645,969 A | * | 2/1987 | Hoffman | 313/487 |
| 4,835,400 A | * | 5/1989 | Wolff | 607/94 |
| 4,882,520 A | * | 11/1989 | Tsunekawa et al. | 362/293 |
| 5,798,608 A | * | 8/1998 | Shaw | 313/489 |
| 5,804,914 A | * | 9/1998 | Ozawa et al. | 313/493 |
| 5,813,752 A | * | 9/1998 | Singer et al. | 313/643 |
| 5,905,333 A | * | 5/1999 | Tomura et al. | 313/485 |
| 6,139,174 A | * | 10/2000 | Butterworth | 362/555 |
| 6,184,618 B1 | * | 2/2001 | Justel et al. | 313/463 |
| 6,208,069 B1 | * | 3/2001 | Justel et al. | 313/487 |
| 6,417,614 B1 | * | 7/2002 | Ronda et al. | 313/485 |
| 6,570,319 B2 | * | 5/2003 | Juestel et al. | 313/485 |
| 6,621,218 B1 | * | 9/2003 | Matsumoto | 313/607 |
| 6,764,501 B2 | * | 7/2004 | Ganz | 607/92 |
| 6,878,154 B2 | * | 4/2005 | Griffith et al. | 607/94 |
| 6,888,302 B2 | * | 5/2005 | Juestel et al. | 313/489 |

FOREIGN PATENT DOCUMENTS

| | | |
|---|---|---|
| DE | 3825535 | 2/1990 |
| EP | 0422474 | 4/1991 |

* cited by examiner

*Primary Examiner*—A. Farah

(57) ABSTRACT

A tanning device is described by which the bluish light emitted by mercury vapor lamps is converted into yellow or white light. For this purpose, the mercury lamps, or the sheets of transparent plastics material covering these lamps, are doped or coated with one or more organic or inorganic fluorescent dyes that partially absorb the blue light emitted by the mercury lamps and convert it into light of wavelengths of 550 to 650 nm.

13 Claims, 4 Drawing Sheets

TANNING DEVICE

The invention relates to a tanning device by which the bluish UV light emitted by mercury-vapor lamps is converted into bright, white light without the tanning effect of the UV light being adversely affected thereby to any substantial extent.

Devices producing UV radiation are known to be used for the cosmetic and therapeutic treatment of the skin. There are known for this purpose face tanners of small area and devices in which a person who is standing or lying down can be irradiated from one or more sides. What are used in particular for whole-body tanning are tanning beds having a tanning surface with a canopy mounted over the top thereof.

Modern-day tanning devices are generally fitted with six low-pressure mercury-vapor lamps in the case of units for facial tanning and with up to fifty low-pressure mercury-vapor lamps in the case of tanning beds, the lamps emitting principally UVA radiation and 0.5 to 5% of UVB radiation. Hence, there is known from German application laid open to public inspection 38 25 535 a UV irradiation device having a gas-discharge source and a phosphor that absorbs the radiation produced by the gas-discharge source and emits longer-wave UV radiation. A planar transparent substrate is coated in this case with a conventional phosphor that is highly absorbent of short-wave UV radiation in the region of approximately 185 nm and 254 nm and emits long-wave UV radiation having a spectrum that exhibits a steep rise in energy in a wavelength range from approximately 310 nm to 360 nm and then a decline in energy in the region of approximately 440 nm.

The CLEO lamps (Natural, Swift, Advantage) that are typically used for this application contain one or two phosphors from the group comprising $SrAl_{12}O_{19}$:Ce (SAC), $LaPO_4$:Ce (LAP) and $BaSi_2O_5$:Pb (BSP). These phosphors emit only UV radiation, their spectra having superimposed on them the Hg lines at 405, 435 and 546 nm. This produces a bluish light from the tanning device that is felt to be unpleasant by the person who wants to be tanned because his or her own skin looks cool and white and hence unhealthy and unnatural.

An attempt has therefore already been made to mask the bluish light from the mercury vapor lamps by incorporating in the tanning device some lamps that are equipped with the $Y_2O_3$:EU (YOX) phosphor and emit red light. This attempt has not, however, been particularly successful, because the light produced in this case is a mixture of red and blue light and thus gives a pink color.

An object that therefore became apparent was to develop a tanning device that no longer radiated the unpleasant bluish light but that instead radiated yellow or white light, without this reducing the tanning effect of the UV radiation to any noticeable extent.

The invention therefore relates to a tanning device in which the mercury vapor lamps emitting the UV light, or the transparent sheets of plastics material covering these lamps, are doped or covered with one or more organic or inorganic fluorescent dyes that partially absorb the bluish light emitted by the mercury lamps, convert it into a longer-wave yellowish or orange light and thus produce a bright, white light.

The conversion of the bluish light emitted by the mercury lamps into a longer-wave white light can be effected by means of special organic or inorganic fluorescent dyes that absorb the mercury-generated light in the wavelength range from 400 to 550 nm and convert it into yellowish or orange light having a wavelength of from 550 to 650 nm. By mixing the bluish and the yellowish or orange components of the light, a bright, white light is obtained.

What have proved successful as organic fluorescent dyes are above all coumarin or perylene dyes such as are known from European patent EP 0 422 474, for example. If these fluorescent dyes are applied to sheets of transparent plastics material, which may be composed of polymethyl methacrylate (PMMA) for example, or are dissolved in the plastics material, there is a change in the spectrum of the light emitted without there being any substantial reduction in the tanning effect.

PMMA sheets exhibit uniform transmission of visible and UV light up to approximately 290 nm. By doping the PMMA sheet with an organic fluorescent dye that absorbs the blue Hg lines at 405 and 435 nm, the emission spectrum can be affected to a wide extent, thus enabling either a cold, a warm white or even an orange-red light to be produced depending on the emission spectrum that the fluorescent dye used has. This provision considerably increases the brightness of the light emitted by the tanning device because the lumen equivalent of white light (~300 lm/W) is far higher that the lumen equivalent of radiation at 405 nm (0.4 lm/W) and 435 nm (12 lm/W). A typical tanning bed comprises fifty tanning lamps each of which has a power of 160 W. This gives a current consumption of 8 kW. A fluorescent lamp converts approximately 3.3% of the electrical power consumed into visible Hg lines at 405, 435 and 546 nm. There is therefore about 260 W of visible light produced, which corresponds to only approximately 3000 lm.

However, the conversion of the said Hg lines into a spectrum of white light giving 300 lm/W produces 54,000 lm, provided that the photoluminescent quantum yield of the color conversion means is approximately 100% and the energy loss (average Stokes shift) is 70%. After dissolution in PMMA or polystyrene (PS), the perylene fluorescent dyes commercially available under the Lumogen® trademark have an efficiency of more than 90%. Hence, a tanning bed will be so strongly illuminated that this will have a decidedly positive effect on the mood of the person intending to tan himself or herself, because bright light is known to lower the melatonin level in the blood. Persons who tan themselves with the tanning device according to the invention will therefore experience a considerable improvement in their mood if they keep their eyes open and wear sunglasses that transmit radiation at above 380 nm. The reduction in the melatonin level in the blood is controlled by the eyes and operates particularly actively when there is radiation in the range between 410 and 430 nm. The brightness of the light from a tanning device according to the invention can of course be increased to a degree that is all the higher the greater the proportion of UV light that is converted into visible light. This does reduce the tanning power of the radiation somewhat but it is possible in this way to obtain a tanning device according to the invention in which the illuminance is more than 100,000 lm.

These and other aspects of the invention are apparent from and will be elucidated with reference to the embodiments described hereinafter.

Figure 1:
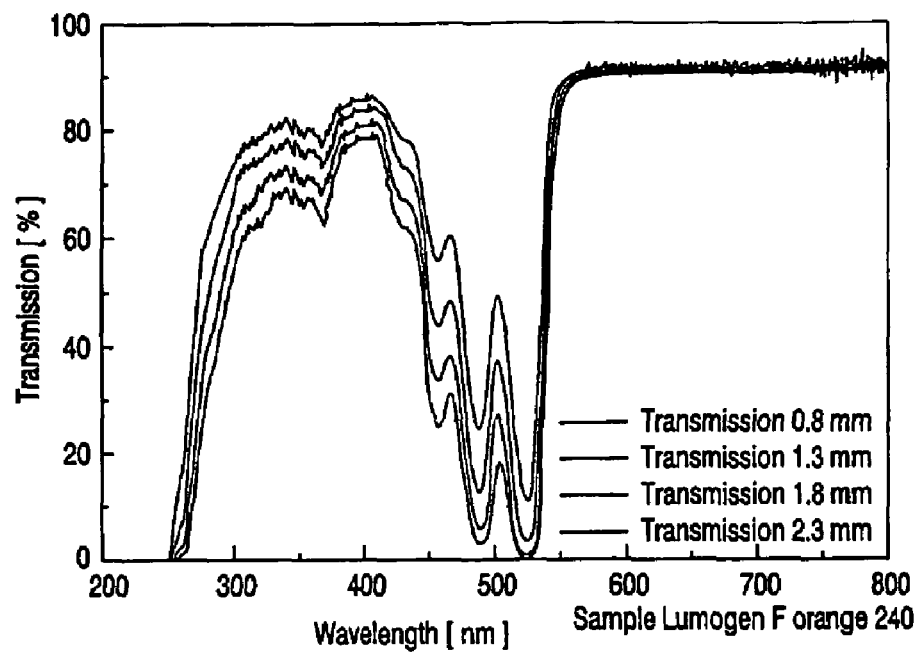
FIG. 1 shows a transmission spectrum for 100 ppm of Lumogen F Orange 240 in PMMA.
Figure 2:
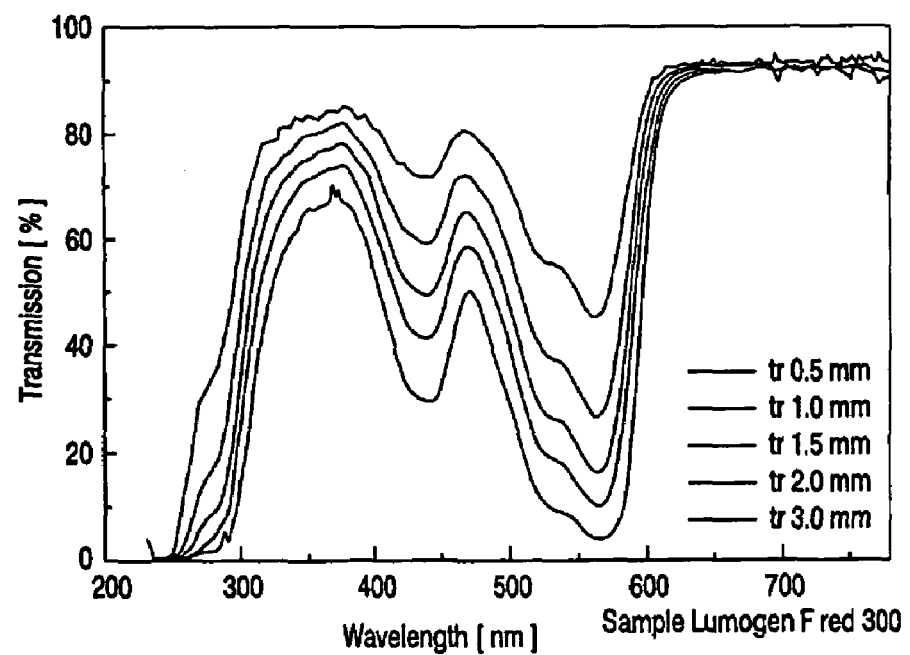
FIG. 2 shows a transmission spectrum for 100 ppm of Lumogen F Red 300 in PMMA.

The following Lumogen® dyes have proved to be particularly suitable for the tanning device according to the invention.

| | | |
|---|---|---|
| Lumogen F Violet 570 | 413 nm | Violet |
| Lumogen F Yellow 083 | 490 nm | Green |
| Lumogen F Yellow ED206 | 518 nm | Yellow |
| Lumogen F Orange 240 | 539 nm | Orange |
| Lumogen F Red 300 | 613 nm | Red |

All Lumogen dyes can easily be dissolved in PMMA or other polymers such as polyethylene, polycarbonate, polystyrene or PVC in a concentration of up to 0.5%, polar polymers such as PMMA being better suited to this than non-polar plastics materials (polyethylene).

Tanning devices that emit a white, tanning radiation rather than the bluish Hg light that was normal hitherto can also be produced by using inorganic fluorescent dyes. With inorganic fluorescent dyes too, part of the bluish Hg lines can be converted into yellow light, thus giving a white spectrum of light from the lamp. This aim can be achieved either by using an individual yellow fluorescent dye or by using a mixture of fluorescent dyes comprising a red and a green fluorescent dye.

What is suitable for producing a yellow light is a fluorescent dye of the composition $(Y_{1-x-y}Gd_x)_3(Al_{1-w}Ga_w)_5O_{12}:Ce_y$ (YAG:Ce).

The mixture of a green and a red fluorescent dye can be produced by mixing $SrGa_2S_4:Eu$ (green 535 nm) with $(Sr_{1-x}Ca_x)S:Eu$ where $0<x<1$ (red 610 to 650 nm).

The fluorescent dye emitting visible light can be applied either to the glass body of the mercury vapor lamp or to a sheet of transparent plastics material covering such lamps. It is particularly useful for the inorganic fluorescent dye to be doped into the polymer material or to be added to a layer of SiO2 that is produced by the sol-gel process from tetraethyl orthosilicate (TEOS).

The brightness of the tanning device is considerably increased in this way in the same way as occurs when, as described above, organic fluorescent dyes are used. The effect of the conversion of the bluish Hg lines by the use of $Y_3Al_5O_{12}:Ce$ as a component of the mixture is shown by the following table

TABLE 1

| YAG:Ce [%] | UVA [W/m$^2$] at a distance of 2 m | UVB [% of UVA] | Erythema < 320 mm [mW/m$^2$] | Erythema > 320 mm [mW/m$^2$] | x value | y value | Lux [lm/m$^2$] | Corr. color temp. [K] | CRI |
|---|---|---|---|---|---|---|---|---|---|
| 0 | 0.652479 | 2.668973 | 1.436577 | 0.52456 | 0.229233 | 0.243694 | 18.20634 | 29700 | 0 |
| 1 | 0.64325 | 2.687246 | 1.426205 | 0.515918 | 0.250091 | 0.27298 | 21.8028 | 16044 | 0 |
| 2 | 0.631017 | 2.705473 | 1.408997 | 0.504904 | 0.274208 | 0.305627 | 26.74236 | 9220 | 0 |
| 3 | 0.615941 | 2.723654 | 1.385176 | 0.491667 | 0.298903 | 0.338235 | 32.98264 | 6736 | 4.9 |
| 4 | 0.598223 | 2.741791 | 1.35506 | 0.47638 | 0.322276 | 0.368507 | 40.4581 | 5460 | 17.3 |
| 5 | 0.578097 | 2.759886 | 1.319058 | 0.459247 | 0.343283 | 0.39527 | 49.08036 | 5160 | 29.2 |
| 6 | 0.555828 | 2.777941 | 1.27766 | 0.440491 | 0.361542 | 0.418185 | 58.74094 | 4214 | 34.9 |
| 7 | 0.521706 | 2.795962 | 2.231424 | 0.420354 | 0.37708 | 0.437414 | 69.31518 | 3992 | 39.9 |
| 8 | 0.506037 | 2.813955 | 1.180969 | 0.399088 | 0.390139 | 0.453353 | 80.66659 | 3810 | 42.7 |
| 9 | 0.479137 | 2.831927 | 1.126953 | 0.376952 | 0.401041 | 0.466478 | 92.65096 | 3658 | 44.4 |

A fluorescent dye having an absorption spectrum as shown in FIG. 1 is particularly well suited to use in a tanning device because not only does it convert the blue or green Hg lines but it is also transparent in that UV range in which the major proportion of the UV radiation is situated. As a function of the absorption of the PMMA sheet, which can be easily altered, it is possible to obtain a transmission of >80% for the sheet in the UV range. The mercury lines at 405 and 436 nm, which are responsible for the bluish light from the tanning device, are used, in accordance with the invention, to a considerable extent for color conversion. The result is that the UV radiation from the fluorescent lamp acts on the person being tanned together with the emission spectrum of the Lumogen dyes. This gives light having a spectrum that causes the human skin to appear in a more agreeable light and that improves the personal impression that the person being tanned has of the tanning effect that has been achieved.

The effect of adding YAG:Ce to the mixture of UV phosphors as described for a CLEO Professional S lamp is shown in table 1 as a function of the concentration of the YAG:Ce.

It can be seen from the above table that adding 4 to 6% of YAG:Ce is enough to produce a pleasant color temperature in the range from 4,000 to 5,500 K, in which case a color rendering index in the range of 20 to 35 can be obtained.

The reduction in the UVA light is less than 20% even at high YAG:Ce contents (5 to 8%), because YAG:Ce hardly absorbs at all in the UVA range.

A similar effect is also obtained when the inorganic fluorescent dye is applied to the glass body of the mercury lamp in the form of an agent doping a layer of $SiO_2$ or a polymer layer.

TABLE 2

| Effective thickness [cm] | UVA [W/m$^2$] at a distance of 2 m | UVB [% of UVA] | Erythema < 320 mm [mW/m$^2$] | Erythema > 320 mm [mW/m$^2$] | x value | y value | Lux [lm/m$^2$] | Corr. color temp. [K] | CRI |
|---|---|---|---|---|---|---|---|---|---|
| 0 | 0.65 | 2.67 | 1.44 | 0.52 | 0.23 | 0.24 | 18.21 | 29700 | 0 |
| 0.0002 | 0.63 | 2.73 | 1.43 | 0.5 | 0.27 | 0.3 | 25.35 | 9566 | 0 |
| 0.0004 | 0.61 | 2.79 | 1.41 | 0.49 | 0.3 | 0.35 | 32.04 | 6398 | 2 |
| 0.0006 | 0.6 | 2.85 | 1.4 | 0.47 | 0.32 | 0.39 | 38.3 | 5340 | 14.3 |
| 0.0008 | 0.56 | 2.9 | 1.39 | 0.45 | 0.34 | 0.41 | 44.16 | 5164 | 23.1 |
| 0.001 | 0.57 | 2.96 | 1.38 | 0.44 | 0.36 | 0.43 | 49.65 | 4108 | 27.1 |
| 0.0012 | 0.55 | 3.01 | 1.37 | 0.42 | 0.37 | 0.45 | 54.78 | 4052 | 30.2 |
| 0.0014 | 0.54 | 3.06 | 1.36 | 0.41 | 0.38 | 0.47 | 56.59 | 3926 | 31.9 |
| 0.0016 | 0.52 | 3.12 | 1.35 | 0.39 | 0.39 | 0.48 | 64.09 | 3829 | 32.9 |
| 0.0018 | 0.51 | 3.16 | 1.34 | 0.38 | 0.4 | 0.49 | 68.32 | 3736 | 33.6 |

The effect of a layer of YAG:Ce applied to the glass body of a mercury lamp, where the mercury lamp conforms to the specification of a CLEO Professional S lamp is shown in Table 2 as a function of the effective thickness of the layer of YAG:Ce.

The invention will be elucidated in detail by the following examples:

EXAMPLE 1

Table-Top Unit Having Six CLEO Performance Lamps that are Covered with a Layer of PMMA Containing Lumogen F Orange 240

The PMMA was dissolved in a mixture of acetone and toluene and Lumogen F Orange was added in a quantity of between 0.05 and 0.02% by weight as a percentage of the PMMA. Six 20 W CLEO Natural lamps were roughened with a jet of sand and then coated with the PMMA/Lumogen F Orange 240 solution. After coating, the lamps were dried and were screwed into a table-tap tanning unit.

Figure 3:
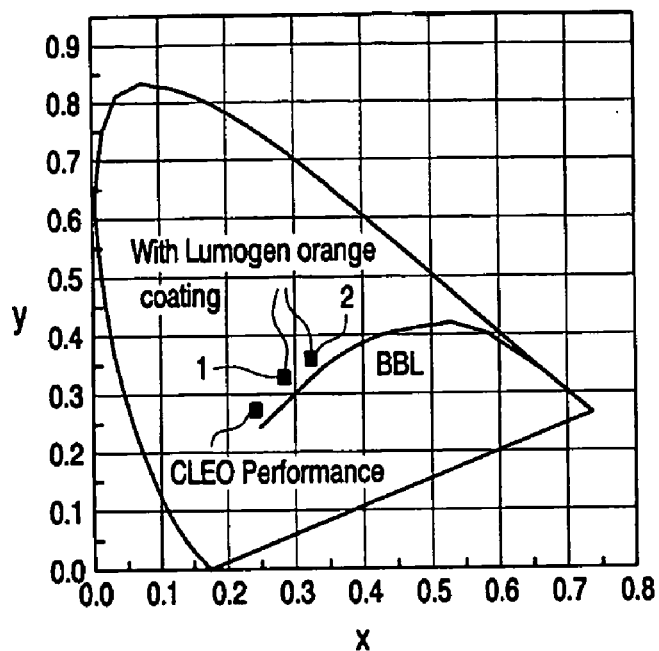
FIG. 3 shows the effect of using a layer of PMMA doped with Lumogen F Orange 300 on the spectrum locus of a CLEO Performance lamp.

The color of the light from the table-top tanning unit moved from x=0.23, y=0.25 (CLEO Performance) to x=0.28, y=0.33 at film thickness 1 (=50 μm) or x=0.31, y=0.36 at film thickness 2 (=100 μm) (see points 2 and 3 in FIG. 3).

The effect of the coating on the specification of the tanning unit is shown by the following table:

|  | CLEO 20 W | Coated lamp envelopes (in accordance with the invention) | Δ [%] |
|---|---|---|---|
| UVA W/m$^2$ | 0.4098 | 0.3660 | −11 |
| UVB W/m$^2$ | 0.0035 | 0.0032 | −9 |
| UVA/UVB % | 0.86 | 0.86 | 0 |
| EryA mW$_{er}$/m$^2$ | 0.31 | 0.27 | −13 |
| EryB mW$_{er}$/m$^2$ | 0.27 | 0.25 | −7 |
| EryTotal mW$_{er}$/m$^2$ | 0.58 | 0.53 | −10 |
| EryB/EryA | 0.87 | 0.93 | +7 |

It can be seen from this table that the coating causes a reduction in the UVA and UVB radiation. Hence, the erythema values, i.e. numerical figures, which express the skin irritation caused by exposure to the UV light, are slightly lower when the lamps coated in accordance with the invention are used than when the prior art uncoated CLEO lamps are used. However, at the same time it can be seen from the right-hand column that the differences in UV radiation and in skin irritation are of the order of approximately 10% and thus show that adequate tanning can still be obtained with the coated lamps, that have the great advantage of not emitting bluish light but bright, white light.

EXAMPLE 2 a) A Tanning Lamp that is Provided with a Luminescing Layer Containing LaPO$_4$:Ce, BaSi$_2$O$_5$:Pb and 5% Y$_3$Al$_5$O$_{12}$:Ce A suspension of butyl acetate containing a mixture of 75% BaSi$_2$O$_5$:Pb, 20% LaPO$_4$:Ce and 5% Y$_3$Al$_5$O$_{12}$:Ce was produced and passed through a screen of 36 μm mesh. By the process known as flow-coating, the suspension was applied to the inner wall of a typical tube of soft glass of the kind used for the manufacture of fluorescent lamps. The viscosity of the suspension was set in such a way that the resulting layer of fluorescent dyes had an average weight of between 0.5 and 3 mg/cm$^2$.

After the coating, the organic components were removed by heating to 550 to 600° C. The lamps were then filled with argon at a few mbar and with 1 to 50 mg of mercury. Finally, the electrodes were inserted in the lamp and the envelope of the lamp was sealed.

Figure 4:
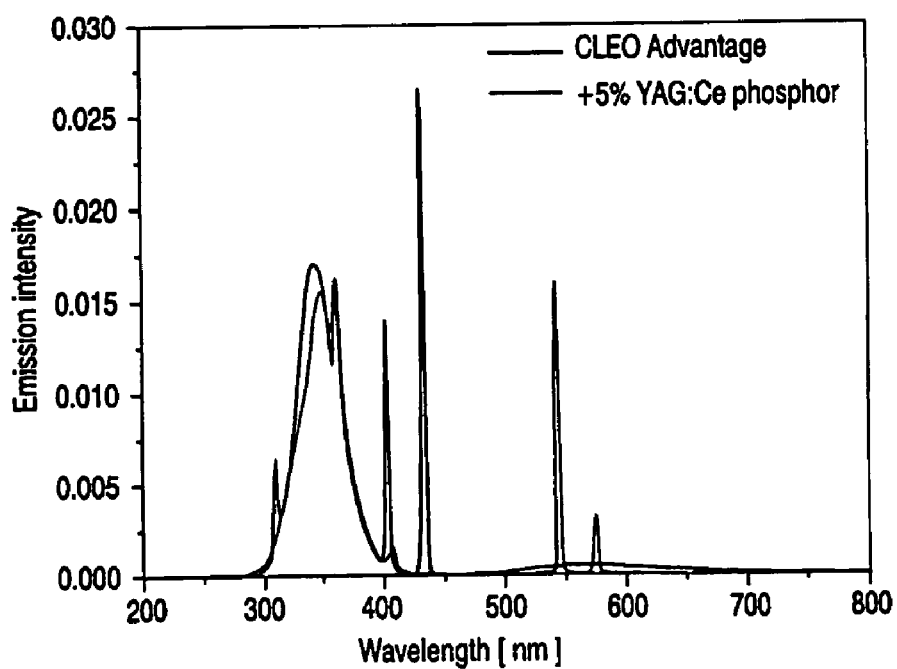
FIG. 4 shows the spectrum of a CLEO Advantage lamp and the spectrum of a lamp according to the invention that has been coated with a layer of $SiO_2$ doped with YAG:Ce.

The shift in the spectrum of a CLEO Advantage lamp that is produced by a lamp according to the invention that has been coated with a layer of SiO$_2$ doped with YAG:Ce is shown in FIG. 4.

Figure 5:
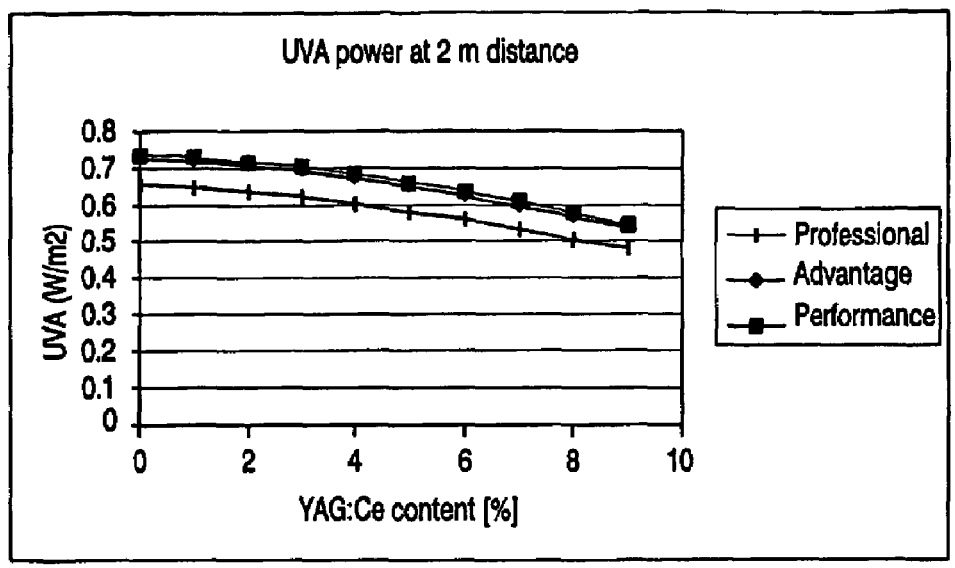
FIG. 5 shows the reduction in the UVA radiation from different CLEO lamps as a function of the YAG:Ce content (in % by weight) of the phosphor layer.

The effect of the quantity of YAG:Ce additive in the layer of phosphor on the reduction of the UV radiation emitted is shown in FIG. 5.

b) Tanning Lamp Having a Layer of Fluorescent Dye Containing LaPO$_4$ and SrAl$_{12}$O$_{16}$:C$_9$ and Covered with a Layer of SiO$_2$ Containing Y$_3$Al$_{15}$O$_{12}$:Ce A layer of SiO$_2$ was applied to a CLEO Professional lamp by the dip-coating or flow-coating process. The suspension for the coating was produced by acid hydrolysis from tetraethyl orthosilicate (TEOS). An SiO$_2$ gel was obtained in this way, to which a few percent by weight of Y$_3$Al$_{15}$O$_{12}$:Ce was added. On completion of the coating operation, the layer was fixed by heat treatment and when this was done the organic constituents were removed.

Figure 6:
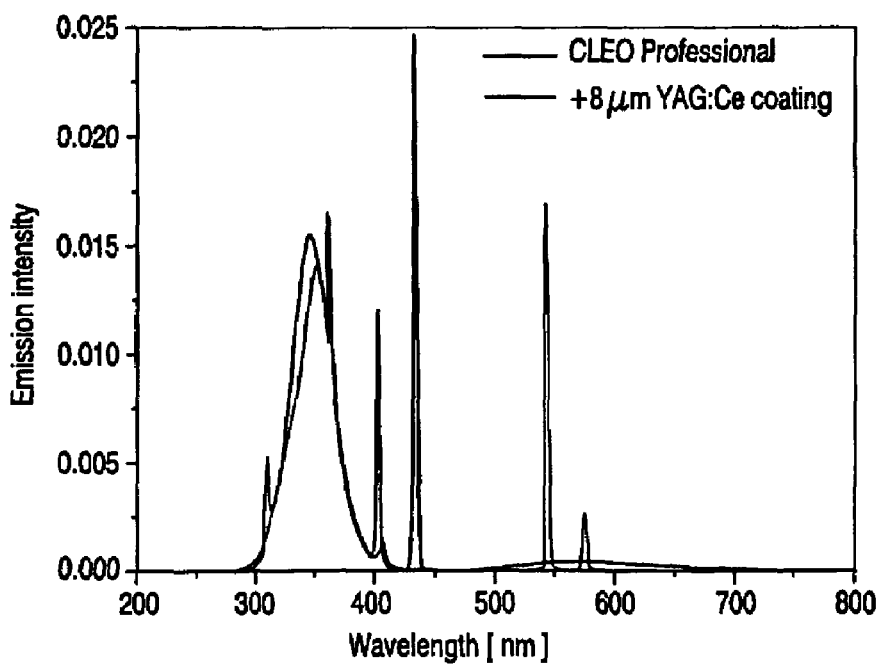
FIG. 6 shows the spectrum of a CLEO Professional lamp and the spectrum of a lamp according to the invention that has been coated with a layer of $SiO_2$ doped with YAG:Ce.

The shift in the spectrum of a CELO Professional lamp that is produced by a lamp according to the invention that has been coated with a layer of SiO$_2$ doped with YAG:Ce is shown in FIG. 6.

Figure 7:
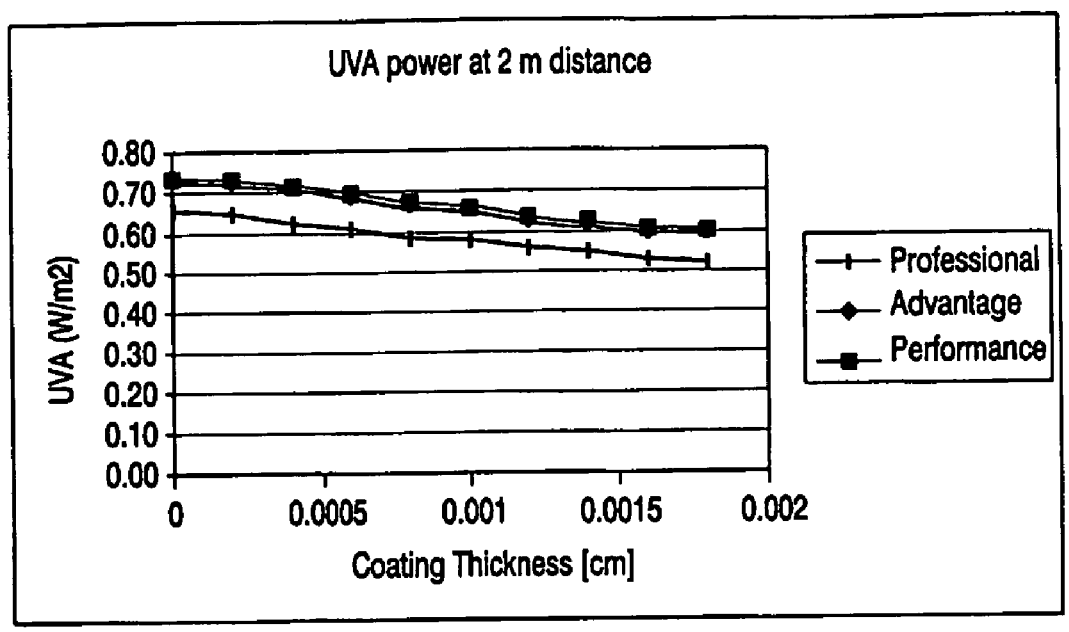
FIG. 7 shows the reduction in the UVA radiation from different CLEO lamps as a function of the optical thickness of the layer of YAG:Ce.

The reduction in UVA radiation with the thickness of the layer of YAG:Ce on different lamps is shown in FIG. 7

The tanning device according to the invention thus does not emit bluish light but a pleasant yellowish or white light, without this causing any noticeable reduction in the tanning effect of the UV radiation.

The invention claimed is:

1. A tanning device, characterized in that a plurality of mercury vapor lamps emitting a UV light, or a plurality of transparent plastics sheets covering the mercury lamps, are doped or covered with one or more organic or inorganic fluorescent dyes that partially absorb the UV light emitted by the mercury lamps, covert it into a longer-wave yellowish light, and thus produce a bright, white light, and
    further characterized in that the sheets of transparent plastics material used to cover the mercury lamps, or a plurality of glass bodies of the mercury lamps, are coated with a layer of $SiO_2$ that contains at least one organic or inorganic fluorescent dye or one of the mixtures thereof.

2. A tanning device as claimed in claim 1, characterized in that what is used as a fluorescent dye is a coumarin or perylene dye that absorbs the mercury-generated light in the wavelength range from 400 to 550 nm and converts it into light having a wavelength of 550 to 650 nm.

3. A tanning device as claimed in claim 1, characterized in that what is used as an inorganic fluorescent dye is at least one compound having the formula $(Y_{1-x-y}Gd_x)_3(Al_{1-w}Ga_w)_5O_{12}:Ce_y$ or $SrGa_2S_4:Eu$ or $(Sr_{1-x}Ca_x)S:Eu$.

4. A tanning device as claimed in claim 1, characterized in that at least one organic or inorganic fluorescent dye or one of the mixtures thereof is contained in the sheet of transparent plastics material that is used to cover the mercury lamps.

5. A tanning device as claimed in claim 1, characterized in that a plurality of glass bodies of the mercury lamps are coated with a polymer that contains at least one organic or inorganic fluorescent dye or one of the mixtures thereof.

6. A tanning device, characterized in that a plurality of mercury vapor lamps emitting a UV light, or a plurality of transparent plastics sheets covering the mercury lamps, are doped or covered with one or more organic fluorescent dyes that partially absorb the UV light emitted by the mercury lamps, covert it into a longer-wave yellowish light, and thus produce a bright, white light, and
    further characterized in that what is used as at least one fluorescent dye includes a coumarin dye that absorbs the mercury-generated light in the wavelength range from 400 to 550 nm and converts it into light having a wavelength of 550 to 650 nm.

7. A tanning device as claimed in claim 6, characterized in that at least one organic or inorganic fluorescent dye or one of the mixtures thereof is contained in the sheet of transparent plastics material that is used to cover the mercury lamps.

8. A tanning device as claimed in claim 6, characterized in that a plurality of glass bodies of the mercury lamps are coated with a polymer that contains at least one organic or inorganic fluorescent dye or one of the mixtures thereof.

9. A tanning device as claimed in claim 6, characterized in that the sheet of transparent plastics material used to cover the mercury lamps, or a plurality of glass bodies of the mercury lamps, are coated with a layer of $SiO_2$ that contains at least one organic or inorganic fluorescent dye or one of the mixtures thereof.

10. A tanning device, characterized in that a plurality of mercury vapor lamps emitting a UV light, or a plurality of transparent plastics sheets covering the mercury lamps, are doped or covered with one or more inorganic fluorescent dyes that partially absorb the UV light emitted by the mercury lamps, covert it into a longer-wave yellowish light, and thus produce a bright, white light, and
    further characterized in that what is used as an inorganic fluorescent dye is at least one compound having the formula $(Y_{1-x-y}Gd_x)_3(Al_{1-w}Ga_w)_5O_{12}:Ce_y$ or $SrGa_2S_4:Eu$ or $(Sr_{1-x}Ca_x)S:Eu$.

11. A tanning device as claimed in claim 10, characterized in that at least one organic or inorganic fluorescent dye or one of the mixtures thereof is contained in the sheet of transparent plastics material that is used to cover the mercury lamps.

12. A tanning device as claimed in claim 10, characterized in that a plurality of glass bodies of the mercury lamps are coated with a polymer that contains at least one organic or inorganic fluorescent dye or one of the mixtures thereof.

13. A tanning device as claimed in claim 10, characterized in that the sheet of transparent plastics material used to cover the mercury lamps, or a plurality of glass bodies of the mercury lamps, are coated with a layer of $SiO_2$ that contains at least one organic or inorganic fluorescent dye or one of the mixtures thereof.

* * * * *